United States Patent [19]

Kawahara et al.

[11] Patent Number: 5,425,943
[45] Date of Patent: Jun. 20, 1995

[54] MODIFIED TPA-CONTAINING INJECTION COMPOSITION HAVING INCREASED SOLUBILITY

[75] Inventors: Masahiro Kawahara, Tsukuba; Yuichiro Hayashi, Ibaraki; Naoki Asakawa, Tsukuba; Sumio Watanabe, Aichi; Yasuo Miyake, Inuyama, all of Japan

[73] Assignee: Eisai Co., Ltd., Tokyo, Japan

[21] Appl. No.: 900,796

[22] Filed: Jun. 22, 1992

Related U.S. Application Data

[63] Continuation of Ser. No. 576,188, Aug. 27, 1990, abandoned, which is a continuation of Ser. No. 230,148, Aug. 9, 1988, abandoned.

[30] Foreign Application Priority Data

Aug. 10, 1987 [JP] Japan .................................. 62-199381

[51] Int. Cl.⁶ ........................ A61K 37/547; C12N 9/50; C12N 9/64
[52] U.S. Cl. .................................. 424/94.3; 424/94.64; 435/219; 435/226
[58] Field of Search ............................. 424/94.3, 94.64; 435/219, 226

[56] References Cited

U.S. PATENT DOCUMENTS

| | | | |
|---|---|---|---|
| 4,244,943 | 1/1981 | Yamahira et al. | 424/94.63 |
| 4,568,544 | 2/1986 | Hasegawa et al. | 435/188 |
| 4,777,043 | 10/1988 | Bennett et al. | 514/970 |
| 4,898,826 | 2/1990 | Duffy et al. | 435/219 |
| 4,935,237 | 6/1990 | Higgins et al. | 435/219 |
| 4,960,702 | 10/1990 | Rice et al. | 435/219 |

FOREIGN PATENT DOCUMENTS

| | | |
|---|---|---|
| 0156169 | 10/1985 | European Pat. Off. . |
| 0196920 | 10/1986 | European Pat. Off. . |
| 0213794 | 3/1987 | European Pat. Off. . |
| 0217379 | 4/1987 | European Pat. Off. . |
| 0227462 | 7/1987 | European Pat. Off. . |
| 0228862 | 7/1987 | European Pat. Off. . |
| 01786 | 5/1984 | WIPO . |

OTHER PUBLICATIONS

Van Zonneveld et al, J. Cell. Biochem 32:169-178 (1986).

*Primary Examiner*—Marian Knode
*Attorney, Agent, or Firm*—Birch, Stewart, Kolasch & Birch

[57] ABSTRACT

An injection composition comprises a pharmacologically effective amount of a modified tPA, 47.5 mM or more of an amino acid or a salt thereof and is improved in view of stability and solubility.

14 Claims, 4 Drawing Sheets

5,425,943

MODIFIED TPA-CONTAINING INJECTION COMPOSITION HAVING INCREASED SOLUBILITY

This is a continuation of Ser. No. 07/576,188, filed Aug. 27, 1990, now abandoned, which is a continuation of application Ser. No. 07/230,148, filed Aug. 9, 1988, now abandoned.

FIELD OF INDUSTRIAL APPLICATION

The present invention relates to a medicinal composition containing a modified tissue plasminogen activator (hereinafter referred to as "modified tPA"). In particular, the present invention relates to an injection composition containing a modified tPA combined with an amino acid or a salt thereof.

PRIOR ART

It is well known that a modified tPA prepared by modifying a natural tPA reacts on plasminogen in vivo to form plasmin, which destroys a fibrin reticulum in a thrombus to dissolve it and, therefore, the modified tPA is useful in the treatment of patients of diseases of a circulatory organ induced by the formation of the thrombus.

However, it is quite difficult to obtain a stable aqueous solution of the modified tPA usable as a medicinal preparation such as an injection, since the modified tPA is a difficultly soluble protein which is easily deactivated. This is a most important problem in the state of the art on the practical applications of the modified tPA.

SUMMARY OF THE INVENTION

Therefore, an object of the present invention is to provide a modified tPA-containing injection composition having increased water solubility and stability so that the composition can be used satisfactorily in medical treatment.

After intensive investigations of the means of increasing the solubility of the modified tPA in water and the stability thereof, the inventors have found that when an amino acid or a salt thereof is incorporated in the modified tPA, the solubility of the modified tPA in water and also the stability thereof are remarkably increased. The present invention has been completed on the basis of this finding.

The present invention provides an injection composition containing a modified tPA characterized in that it further contains an amino acid or a salt thereof.

An injection composition of the invention comprises a pharmacologically effective amount of a modified tPA, 20 mM or more of an amino acid or a salt thereof and a pharmacologically acceptable carrier.

The amino acids used in the present invention include basic, acidic and neutral amino acids. They can be used either singly or in combination of two or more of them.

The basic amino acids and salts thereof usable in the present invention include arginine, histidine, lysine, ornithine and salts thereof with an inorganic or organic acid (such as those derived from acidic amino acids). The salts include, for example, hydrochloride, acetate, aspartate and glutamate.

The acidic amino acids and salts thereof usable in the present invention include glutamic acid, aspartic acid and salts thereof such as sodium glutamate and sodium aspartate.

The neutral amino acids usable in the present invention include, for example, glycine, alanine, valine, leucine, isoleucine, serine and threonine.

To increase the stability of the composition of the present invention, arginine or a salt thereof is preferably used.

The amount of the amino acid or salt thereof in the composition of the present invention is preferably at least 20 mM.

The modified tPA's used in the present invention include, for example:

(1) mutant tPA prepared by eliminating F and G regions of natural tPA and replacing Gly and Ser at amino acid positions Nos. 183 and 186, respectively, with Ser and Thr, respectively, (2) mutant tPA prepared by eliminating F and G regions of natural tPA and replacing Ser at an amino acid position No. 119 thereof with Met., (3) mutant tPA prepared by eliminating F, G and $K_2$ regions of natural tPA and replacing Ser at an amino acid position No. 119 thereof with Met, (4) mutant tPA prepared by replacing $K_1$ region of natural tPA with $K_1$ region of plasminogen, and (5) mutant tPA prepared by replacing Cys at an amino acid position No. 84 of natural tPA with Ser.

Standard ranges of regions are shown by amino acid position Nos. and amino-acids at these positions in the amino acid sequence of natural tPA. F region ranges from No. 4 (Val) to No. 50 (Ser), G region ranges from No. 51 (Cys) to No. 86 (Ile), $K_1$ region ranges from No. 87 (Asp) to No. 174 (Ser) and $K_2$ region ranges from No. 175 (Glu) to No. 262 (Ser). However, it is to be noted that these ranges are nothing but median examples of the positions and ranges in the respective regions and they by no means limit the ranges of the regions in the present invention.

Particularly selecting No. 4 (Val) to No. 50 (Ser) as the F region, No. 51 (Cys) to No. 86 (Ile) as the G region, No. 87 (Asp) to No. 174 (Ser) as the $K_1$ resion and No. 175 (Glu) to No. 262 (Ser) as the $K_2$ resion, the mutant tPA's corresponding to the above-mentioned items (1), (2), (3), (4) and (5) will be referred to as tPA (2660), tPA (2663), tPA (2810), tPA (8000) and tPA (9200), respectively.

As for the form of the injection composition of the present invention, included not only is a solid or aqueous composition containing both of the modified tPA and the amino acid or salt thereof but also a two-pack type composition comprising a pack of the modified tPA and another pack of the amino acid or a salt thereof, such as an injection composition to be prepared in situ which comprises a vial containing a lyophilized, modified tPA and an ampoule of a solvent containing the amino acid or salt thereof.

The composition of the present invention may contain adjuvants ordinarily used in the production of medicinal preparations such as a filler, stabilizer, buffering agent and isotonizing agent.

The effects of the amino acids and salts thereof in increasing the solubility of the modified tPA in water were confirmed by the following Experimental Examples 1 and 2.

BRIEF DESCRIPTION OF DRAWINGS

FIGS. 1 to 6 are graphs showing the results of Experimental Example 1, wherein FIG. 1 shows the results of the control obtained without army amino acid, FIG. 2 shows those obtained with 3% of L-arginine hydrochloride, FIG. 3 shows those obtained with 3% of L-histidine hydrochloride, FIG. 4 shows those obtained with 3% of sodium L-aspartate, FIG. 5 shows those obtained with 3% of sodium L-glutamate and FIG. 6 shows those obtained with 3% of L-glycine and those obtained with 3% of L-alanine.

FIGS. 8 and 9 are graphs showing the results of Experimental Example 3, wherein FIG. 8 shows the results of the control free of L-arginine-L-aspartate and FIG. 9 shows those obtained with L-arginine-L-aspartate.

EXPERIMENTAL EXAMPLE 1

100 to 200 μg of each of the modified tPA (2663), tPA (8000) and tPA (9200) was placed in a small reaction tube. 10 to 100 μl of a 3% aqueous solution of L-arginine hydrochloride, L-histidine hydrochloride, sodium L-aspartate, sodium glutamate, L-glycine or L-alanine having a pH adjusted to 5.0 to 7.0 was added thereto and mixed thoroughly. The mixture was centrifuged. A specified amount of the supernatant liquid was sampled and subjected to high-performance liquid chromatography to determine the solubility thereof.

A mixture of the modified tPA with a phosphate/citrate buffer solution (McIlvaine buffer) adjusted to pH 5.0 or 7.0 which was free of any amino acid or salt thereof was used as a control to determine its solubility in the same mariner as that described above.

The results are shown in FIGS. 1 to 6.

Figure 2:
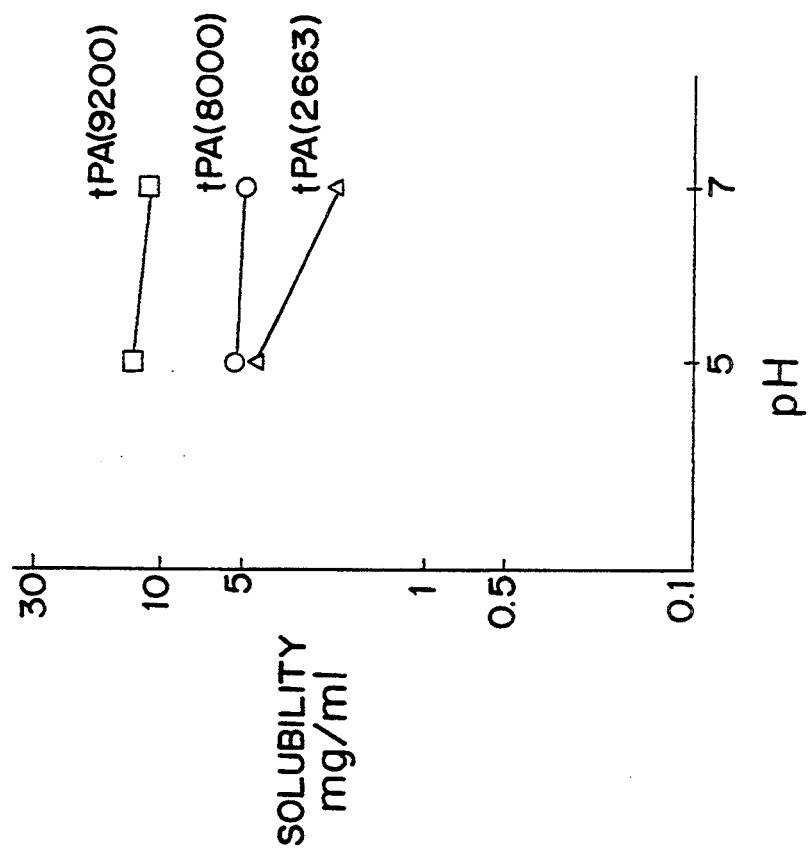
Figure 1:
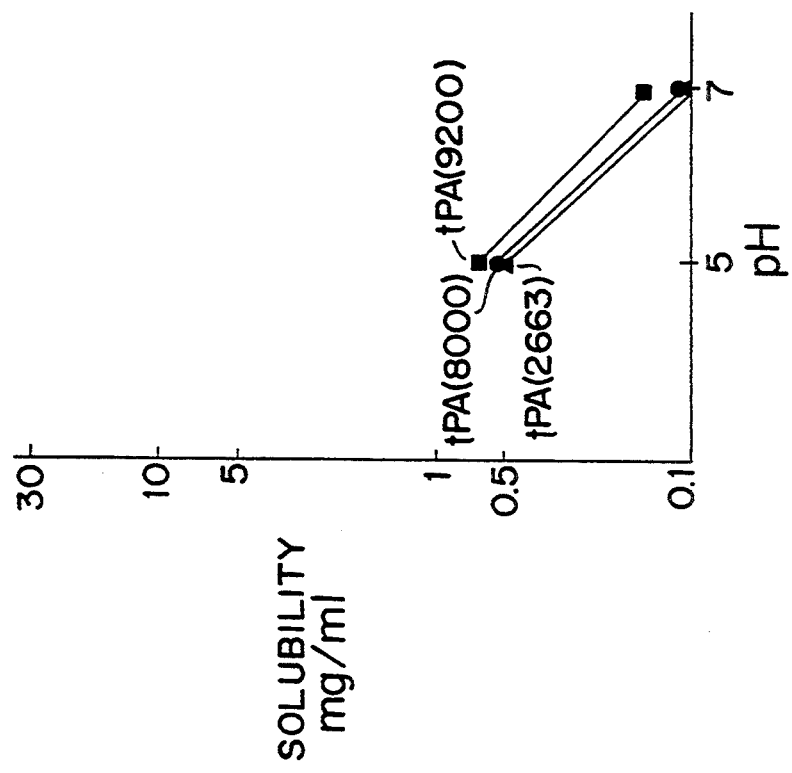
Figure 4:
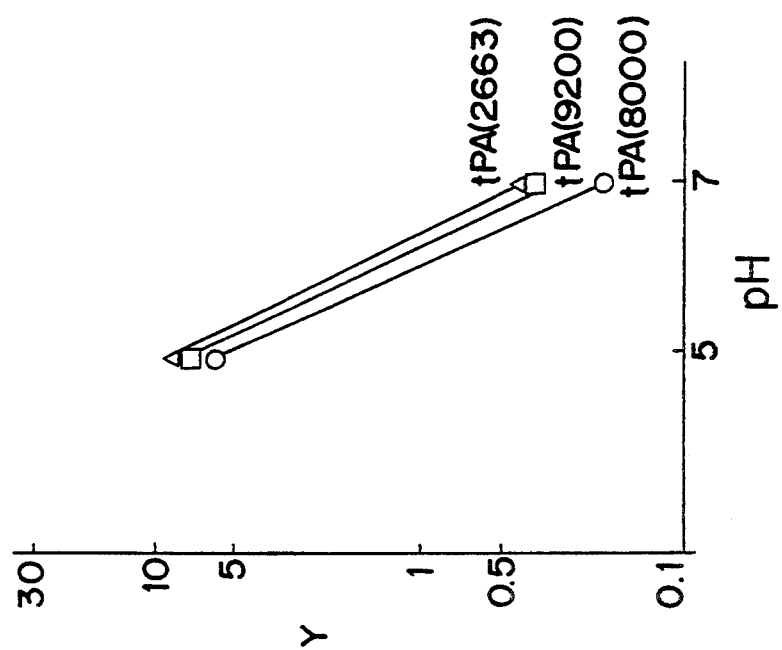
Figure 3:
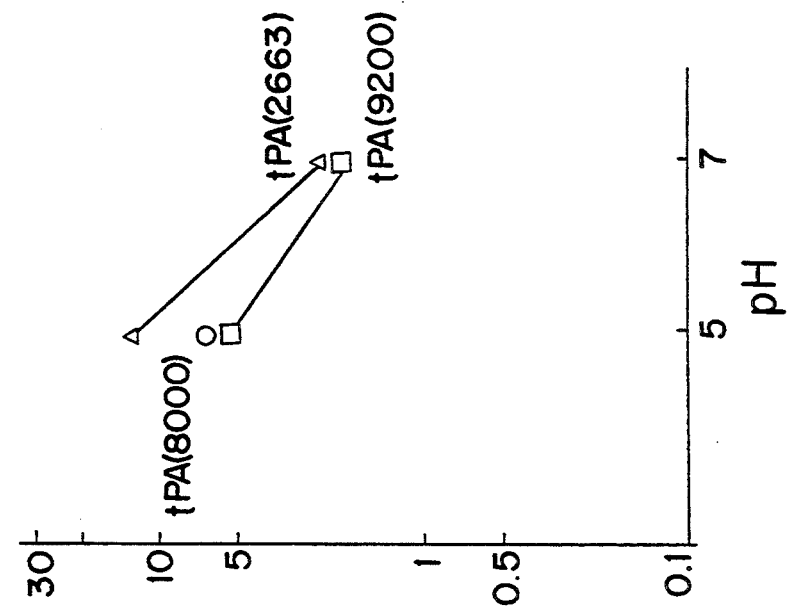
Figure 5:
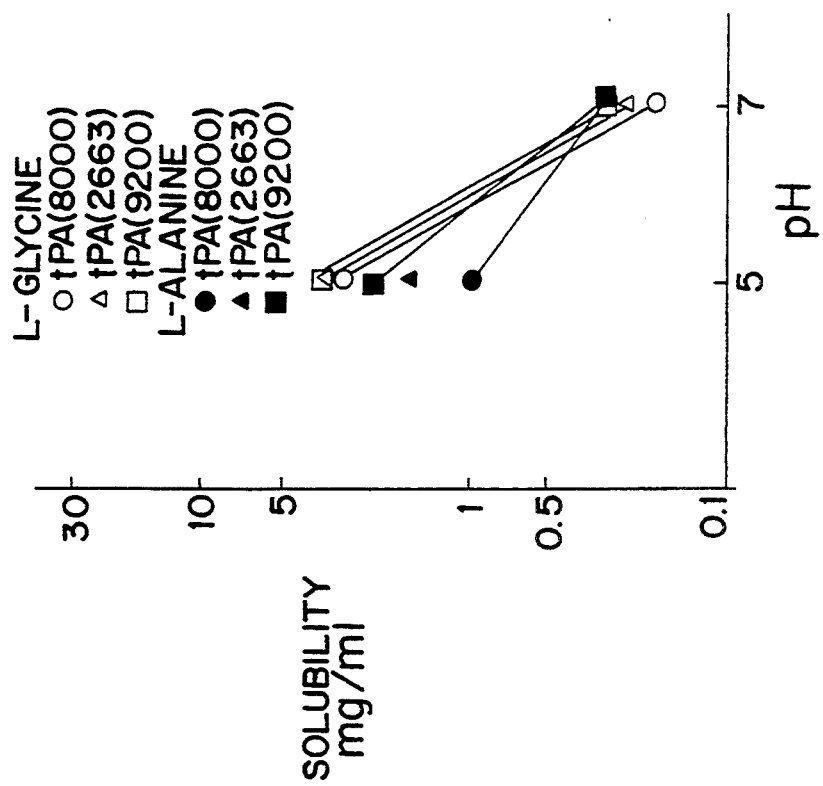
Figure 6:
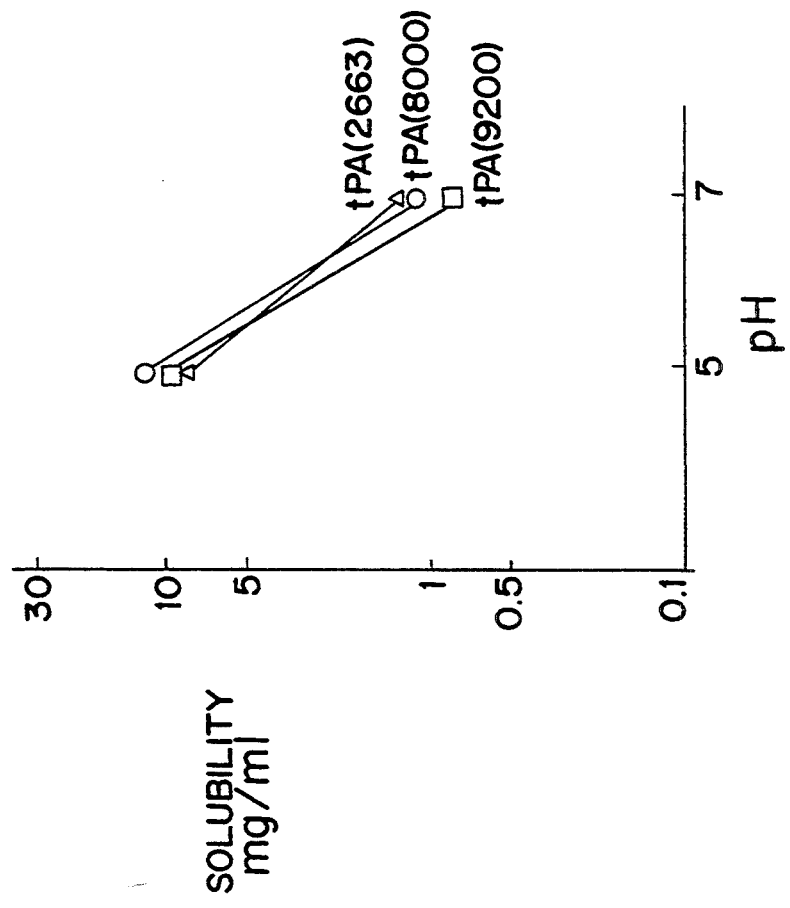

FIG. 1 shows the results obtained with the amino acid-free control. FIG. 2 shows the results obtained with 3% of L-arginine hydrochloride. FIG. 3 shows those obtained with 3% of L-histidine hydrochloride. FIG. 4 shows those obtained with 3% of sodium L-aspartate. FIG. 5 shows those obtained with 3% of sodium L-glutamate. FIG. 6 shows those obtained with 3% of L-glycine and those obtained with 3% of L-alanine.

It is apparent from the results shown in FIGS. 1 to 6 that the amino acids and salts thereof of the present invention remarkably increase the solubility of the modified tPA in water.

EXPERIMENTAL EXAMPLE 2

In order to confirm the influences of the concentration of the amino acids and salts thereof exerted on the solubility of the modified tPA, the same experiments as those of Experimental Example 1 were repeated except that L-arginine hydrochloride was selected as the typical compound and that 1, 2, 3, 5 and 7% aqueous solutions thereof were used.

Figure 7:
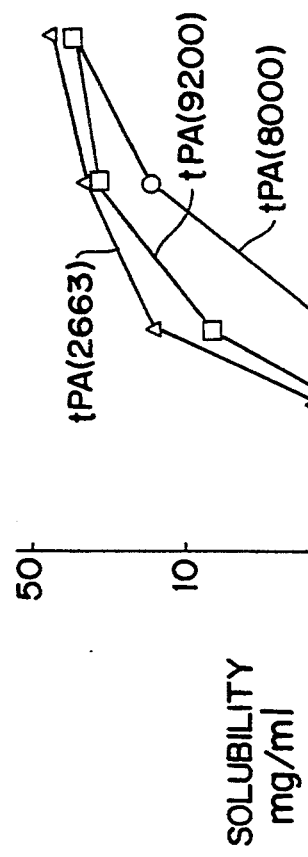
FIG. 7 is a graph showing the results of Experimental Example 2.

The results are shown in FIG. 7.

It is apparent from FIG. 7 that the higher the concentration of L-arginine hydrochloride, the higher the solubility of the modified tPA.

The effects of the amino acids and salts thereof in increasing the stability of the modified tPA were confirmed by the following Experimental Example 3.

EXPERIMENTAL EXAMPLE 3

3 g of L-arginine L-aspartate and 5 g of mannitol were dissolved in 80 ml of distilled water for injection. The pH of the solution was adjusted to 5.0 or 7.0. The distilled water for injection was further added to the solution to make up the total quantity of 100 ml, which was filtered under sterile conditions to obtain a solution to be used as the solvent.

3 mg of each of the modified tPA (2660), tPA (2663), tPA (2810), tPA (8000) and tPA (9200) was dissolved in 10 ml of the solvent prepared above. The solution was filtered under sterile conditions. The filtrate was poured into vials each in an amount of 1 ml and lyophilized. The vials were sealed and stored in a freezer at −20° C., at a cold place (5° C.) or in a thermostatted bath at 45° C. for one month.

After one month, 1 ml of distilled water for injection was poured in each of the stored sample to obtain a solution. The activity of the modified tPA was determined by the clotlysis method and the rate of residual activity was calculated as compared with that of the sample kept in the freezer at −20° C. as the control.

Separately, lyophilized, modified tPA's were prepared in the same manner as that described above except that L-arginine-L-aspartate was omitted. The L-arginine-L-aspartate-free products thus prepared were used as the controls and stored at the same temperature for the same period of time as those specified above to determine the activities and the rates of residual activity thereof in the same manner as that described above.

Figure 8:
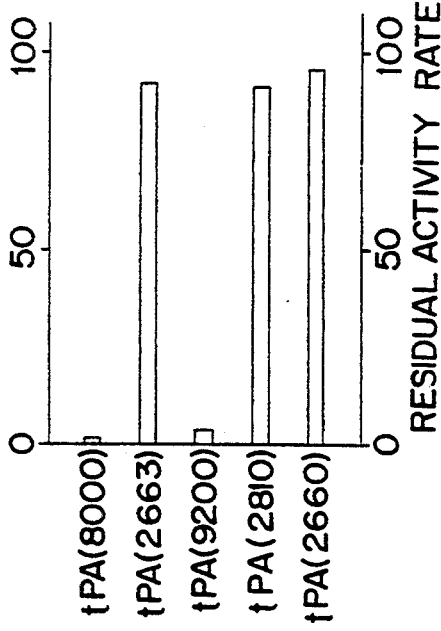
Figure 9:
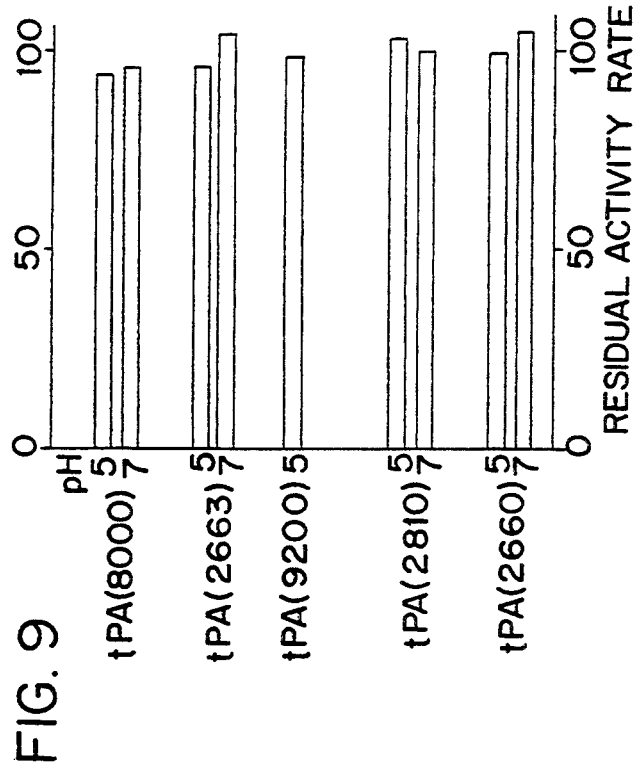

The results are shown in FIGS. 8 and 9.

FIG. 8 shows the results obtained without L-arginine-L-aspartate and FIG. 9 shows those obtained with L-arginine-L-aspartate.

It is apparent from the results of FIGS. 8 and 9 that the amino acids and salts thereof according to the present invention remarkably increase the stability of the modified tPA.

EXAMPLES

The following Examples will further illustrate the present invention, which by no means limit the invention.

EXAMPLE 1

500 mg of L-arginine hydrochloride and 500 mg of mannitol were dissolved in 8 ml of distilled water for injection. The pH of the solution was adjusted to 5.0. 30 mg of the modified tPA (8000) was dissolved in the solution. Distilled water for injection was added to the solution to make up the total quantity of 10 ml. The solution was filtered under sterile conditions and poured in vials each in an amount of 1 ml and lyophilized. The vials were sealed.

Separately, ampoules each containing, as the solvent, 1 ml of distilled water for injection were prepared.

EXAMPLE 2

500 mg of L-arginine-L-aspartate and 500 mg of mannitol were dissolved in 8 ml of distilled water for injection. The pH of the solution was adjusted to 5.5. 30 mg of the modified tPA (9200) was dissolved in the solution. Distilled water for injection was added to the solution to make up the total quantity of 10 ml. The solution was filtered under sterile conditions, poured in vials each in an amount of 1 ml and lyophilized. The vials were sealed.

Separately, ampoules each containing, as the solvent, 1 ml of distilled water for injection were prepared.

EXAMPLE 3

30 mg of the modified tPA (2663) prepared under sterile conditions was homogeneously mixed with 500 mg of sterile mannitol and the mixture was placed in vials each in such an amount that 5 mg of the modified tPA (2663) would be contained in each vial. The vials were sealed.

Separately, 500 mg of sodium L-glutamate was dissolved in distilled water for injection to obtain 10 ml of a solution. The pH of the solution was adjusted to 5.0. The solution was poured in ampoules each in an amount of 1 ml to obtain ampoules of the solvent.

EXAMPLE 4

5 g of L-arginine-L-aspartate and 5 g of mannitol were dissolved in 80 ml of distilled water for injection. The pH of the solution was adjusted to 5.0. 200 mg of the modified tPA (2810) was dissolved in the solution. Distilled water for injection was added to the solution to make up the total quantity of 100 ml. The solution was filtered under sterile conditions poured in vials each in an amount of 1 ml and lyophilized. The vials were sealed.

Separately, ampoules each containing, as the solvent, 1 ml of distilled water for injection were prepared.

EXAMPLE 5

300 mg of L-arginine hydrochloride, 50 mg of L-aspartic acid and 500 mg of mannitol were dissolved in 8 ml of distilled water for injection. The pH of the solution was adjusted to 7.0. 50 mg of the modified tPA (2660) was dissolved in the solution. Distilled water for injection was added to the solution to make up the total quantity of 10 ml. The solution was filtered under sterile conditions, poured in vials each in an amount of 1 ml and lyophilized. The vials were sealed.

Separately, ampoules each containing, as the solvent, 1 ml of distilled water for injection were prepared.

We claim:

1. An injection composition comprising:
   (a) a pharmacologically effective amount of a modified tPA selected from the group consisting of:
      (i) a mutant tPA prepared by eliminating regions F and G of natural tPA and replacing Ser at an amino acid position No. 119 thereof with Met,
      (ii) a mutant tPA prepared by replacing $K_1$ region of natural tPA with $K_1$ region of plasminogen, and
      (iii) a mutant tPA prepared by replacing Cys at an amino acid position No. 84 of natural tPA with Ser;
   (b) at least 47.5 mM of a basic or acidic amino acid, a salt thereof, or mixture thereof; and
   (c) a pharmaceutically acceptable carrier.

2. The injection composition as claimed in claim 1, wherein said modified tPA is the mutant tPA prepared by replacing Cys at an amino acid position No. 84 of natural tPA with Ser.

3. The injection composition as claimed in claim 1, wherein said basic amino acid is selected from the group consisting of arginine, histidine, lysine, ornithine and a salt thereof.

4. The injection composition as claimed in claim 1, wherein said acidic amino acid is selected from the group consisting of glutamic acid, aspartic acid and a salt thereof.

5. The injection composition as claimed in claim 1, in which the modified tPA is a mutant tPA prepared by replacing Cys at an amino acid position No. 84 of natural tPA with Ser and the amino acid is a mixture of arginine or a salt thereof and aspartic acid or a salt thereof.

6. The injection composition as claimed in claim 1, wherein said modified tPA is the mutant tPA prepared by replacing Cys at an amino acid position No. 84 of natural tPA with Ser and said amino acid salt is arginine aspartate.

7. The injection composition according to claim 6, wherein the concentration of said amino acid is at least 142.5 mM.

8. The injection composition according to claim 1, wherein said amino acid is selected from the group consisting of L-arginine, L-histidine, L-aspartate, L-glutamate, L-glycine, salts thereof, and mixtures thereof.

9. The injection composition according to claim 8, wherein said amino acid is selected from the group consisting of L-arginine hydrochloride, L-histidine hydrochloride, sodium L-aspartate, sodium L-glutamate, and L-arginine-L-aspartate.

10. The injection composition according to claim 8, wherein the concentration of said amino acid is at least 142.5 mM.

11. The injection composition according to claim 1, wherein the concentration of said amino acid is at least 142.5 mM.

12. The injection composition according to claim 1, wherein the concentration of said amino acid is 95 mM.

13. The injection composition according to claim 1, wherein the pH of the composition is in the range of 5 to 7.

14. An injection composition comprising:
   (a) a pharmacologically effective amount of a mutant tPA prepared by replacing Cys at an amino acid position No. 84 of natural tPA with Ser;
   (b) at least 47.5 mM of L-arginine-L-aspartate; and
   (c) a pharmaceutically acceptable carrier.

* * * * *